United States Patent
Forge et al.

(10) Patent No.: US 9,550,810 B2
(45) Date of Patent: Jan. 24, 2017

(54) BIODEGRADABLE ELECTROCONDUCTING NANOWIRE, METHOD OF MANUFACTURE AND USES THEREOF

(75) Inventors: Vincent Forge, Vourey (FR); Christophe Horvath, Loisin (FR); Marc Fontecave, Saint Ismier (FR); Nicolas Duraffourg, Vinay (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 446 days.

(21) Appl. No.: 14/003,560

(22) PCT Filed: Mar. 6, 2012

(86) PCT No.: PCT/EP2012/053824
§ 371 (c)(1),
(2), (4) Date: Feb. 10, 2014

(87) PCT Pub. No.: WO2012/120013
PCT Pub. Date: Sep. 13, 2012

(65) Prior Publication Data
US 2014/0148575 A1  May 29, 2014

(30) Foreign Application Priority Data

Mar. 7, 2011 (FR) ..................... 11 51851

(51) Int. Cl.
C07K 14/00 (2006.01)
B82Y 30/00 (2011.01)
C07K 14/47 (2006.01)
B82Y 40/00 (2011.01)

(52) U.S. Cl.
CPC ............. C07K 14/001 (2013.01); B82Y 30/00 (2013.01); B82Y 40/00 (2013.01); C07K 14/4711 (2013.01); C07K 2319/735 (2013.01)

(58) Field of Classification Search
None
See application file for complete search history.

(56) References Cited

FOREIGN PATENT DOCUMENTS

WO  2005118633 A2  12/2005

OTHER PUBLICATIONS

Baldwin, A., et al., "Cytochrome Display on Amyloid Fibrils", "J. Am. Chem. Soc.", Jan. 26, 2006, pp. 2162-2163, vol. 128.
Balguerie, A., et al., "Domain organization and structure-function relationship of the HET-s prion protein of Podospora anserina", "The EMBO Journal", 2003, pp. 2071-2081, vol. 22, No. 9.
Baxa, U., et al., "Structure, Function, and Amyloidogenesis of Fungal Prions: Filament Polymorphism and Prion Variants", "Advances in Protein Chemistry", 2006, pp. 125-180, vol. 73.
Blondin, G., et al., "Interplay of Electron Exchange and Electron Transfer in Metal Polynuclear Complexes in Proteins or Chemical Models", "Chemical Reviews", Dec. 1990, pp. 1359-1376, vol. 90, No. 8.
Del Mercato, L., et al., "Charge transport and intrinsic fluorescence in amyloid-like fibrils", "PNAS", Nov. 13, 2007, pp. 18019-18024, vol. 104, No. 46.
Hamedi, M., et al., "Electrochemical Devices Made from Conducting Nanowire Networks Self-Assembled from Amyloid Fibrils and Alkoxysulfonate PEDOT", "Nano Letters", May 9, 2008, pp. 1736-1740, vol. 8, No. 6.
Jones, C., et al., "In vitro assessments of nanomaterial toxicity", "Advanced Drug Delivery Reviews", Apr. 19, 2009, pp. 438-456, vol. 61.
Kasotakis, E., et al., "Design of Metal-Binding Sites Onto Self-Assembled Peptide Fibrils", "Biopolymers", Feb. 18, 2009, pp. 164-172, vol. 92, No. 3.
Lubner, C., et al., "Wiring Photosystem I for Direct Solar Hydrogen Production", "Biochemistry", Nov. 30, 2009, pp. 404-414, vol. 49.
Maddelein, M., et al., "Amyloid aggregates of the HET-s prion protein are infectious", "PNAS", May 28, 2002, pp. 7402-7407, vol. 99, No. 11.
Padalkar, S., et al., "Protein-templated semiconductor nanoparticle chains", "Nanotechnology", May 28, 2008, pp. 1-9, vol. 19, No. 275602.
Dos Reis, S., et al., "The HET-s Prion Protein of the Filamentous Fungus Podospora anserina Aggergates in Vitro into Amyloid-like Fibrils", "J. Biol. Chem.", Dec. 3, 2001, pp. 5703-5706, vol. 277, No. 8.
Sabate, R., et al., "On the binding of Thioflavin-T to HET-s amyloid fibrils assembled at pH 2", "Journal of Structural Biology", Mar. 4, 2008, pp. 387-396, vol. 162.
Scheibel, T., et al., "Conducting nanowires built by controlled self-assembly of amyloid fibers and selective metal deposition", "PNAS", Apr. 15, 2003, pp. 4527-4532, vol. 100, No. 8.
Sipe, J., et al., "Review: History of the Amyloid Fibril", "Journal of Structural Biology", 2000, pp. 88-98, vol. 130.
Taber, A., et al., "Development and Characterization of Conductive Amyloid Fibril Nanowires", "American Chemical Society 64th Northwest Regional Meeting (NORM 2009)", Jun. 29, 2009, Page(s) (Abstract), Accessed via http://acs.confex.com/acs/norm09/webprogram/Paper72881.htm, Published in: Tacoma, WA.

*Primary Examiner* — Anand Desai
(74) *Attorney, Agent, or Firm* — Hultquist, PLLC; Mary B. Grant

(57) ABSTRACT

The subject matter of the invention is an electroconducting nanowire, comprising an amyloid fiber which results from the self-assembling of peptides comprising a prion domain or a derivative of this domain and which is functionalized by electron transporting peptides, each comprising amino acids bound to one or more atoms of iron.

Its subject matter is also a method of manufacturing this nanowire as well as the uses of said nanowire.

Uses: manufacture of sensors for the detection of chemical or biological species, of nano-batteries, of radio-identification systems, of molecular memory systems, etc.

7 Claims, 3 Drawing Sheets

BIODEGRADABLE ELECTROCONDUCTING NANOWIRE, METHOD OF MANUFACTURE AND USES THEREOF

CROSS-REFERENCE TO RELATED APPLICATIONS

This application is a U.S. national phase under the provisions of 35 U.S.C. §371 of International Patent Application No. PCT/EP12/53824 filed Mar. 6, 2012, which in turn claims priority of French Patent Application No. 11 51851 filed Mar. 7, 2011. The disclosures of such international patent application and French priority patent application are hereby incorporated herein by reference in their respective entireties, for all purposes.

TECHNICAL FIELD

The present invention belongs to the technical field of electroconducting nanowires, their manufacture and their uses.

More specifically, it relates to nanowires which, apart from having electrical conduction properties, are biodegradable, in other words that they may be entirely degraded by living organisms, and are provided with self-organisation properties on both a nanoscopic and macroscopic scale.

The invention also relates to a method making it possible to manufacture said nanowires as well as to the uses of said nanowires.

Given their remarkable properties, the nanowires according to the invention are likely to find numerous applications, both nanoscopic and macroscopic.

For instance, they may in particular be used in sensors, and in particular sensors intended to detect chemical or biological species, in nanobatteries, and in particular in nanobatteries intended to transform solar energy into electricity, in radio-identification systems and in all applications of molecular electronics such as, for example, the manufacture of molecular memory systems.

PRIOR ART

The challenge of miniaturisation and the search for new materials with original properties have led technology to enter the nanometric scale.

Thus, numerous works have been dedicated over recent years to the conception and to the production of nano-objects, in other words objects in which one at least of the dimensions is comprised between 1 and 100 nm.

Due to their very small size, nano-objects generally have original properties compared to objects of same chemical composition but of larger size so that their applications are potentially very numerous and cover extremely varied fields such as electronics, microelectronics, optics, medicine, pharmacy, cosmetics, automobiles, aeronautics, etc.

Nevertheless, these nano-objects raise numerous questions in terms of public health.

In fact, it is known that they can enter the body through cutaneous, digestive and respiratory routes, and their presence in cellular tissues could prove, in the long term, to be dangerous and all the more so in that the nano-objects proposed to date are not biodegradable or, in the very best of cases, are only very partially biodegradable.

As regards electroconducting nanowires, which represent a particular category of nano-objects, carbon nanotubes, inorganic nanowires, conducting polymer nanowires, redox polymer nanowires and hybrid organic/inorganic nanowires have been proposed to date.

Carbon nanotubes are constituted of one or more graphite carbon sheets wound round themselves which thus form a cylinder. They may be obtained by creating an electric arc on a carbon electrode or by chemical vapour deposition, better known by the acronym CVD. Thoroughly studied since their invention, carbon nanotubes have electrical conduction properties that vary as a function of their structural characteristics, excellent mechanical strength, good thermal conductivity, large grafting capacity and non-linear optical properties. But initial toxicity studies carried out on animals show that they could induce in humans lesions analogous to those caused by asbestos (Jones and Grainger, *Advanced Drug Delivery Reviews* 2009, 61(6), pages 438-456, [1]).

Inorganic nanowires are constituted of metals such as gold, platinum or nickel, metalloids such as silicon or germanium, metal oxides such as zinc oxide, or metal/metalloid alloys such as gallium arsenide. They are typically formed by growth on the surface of a substrate by CVD. A network of nanowires arranged perpendicularly to the surface of the substrate is thereby formed, which has the advantage of being able to be directly integrated in devices of the field effect transistor type, sensors or analogous. These inorganic nanowires are obviously not biodegradable.

The nanowires of conducting polymers are formed of a sequencing of aromatic monomers of thiophene type or analogous, along which the electrons of the double bonds can move and create an electric current. Conducting polymers stem from the polymers industry and may be manufactured in large quantities. On the other hand, not only are they not biodegradable, they are deprived of self-organisation properties, nevertheless quasi-indispensable for a use of nanowires at a nanoscopic scale. There exists moreover little data in the literature on potential nanoscopic applications of this type of nanowire.

The nanowires of redox polymers are, like the preceding, formed of a sequencing of aromatic monomers but on which are grafted in a regular manner redox centres which can accept or donate an electron by changing oxidation state. Thus, an electron may be donated by one redox centre and accepted by another, which allows it to move along the nanowire by successive jumps from redox centre to redox centre. Apart from the mode and the quality of the electronic transport, the nanowires of redox polymers have the same advantages and the same drawbacks as the nanowires of conducting polymers evoked previously. In particular, they are not biodegradable and their applications are almost exclusively macroscopic.

As for hybrid organic/inorganic nanowires, they are obtained by binding, by covalent bonds or by electrostatic interactions, metal colloids at several places of DNA strands or amyloid fibres and by making metal grow on these colloids until the latter enter into contact with each other and are capable of ensuring an electrical conduction at the surface of said DNA strands or of said amyloid fibres. A metal sheath is thereby created around the DNA strands or amyloid fibres, which must be sufficiently thick to ensure a satisfactory electrical conduction. These nanowires are thus comparable to inorganic nanowires whether in terms of electrical conductivity, solidity and stability but also as regards their incapacity to be degraded by living organisms.

In view of the above, the Inventors set themselves the general aim of supplying nanowires which, while being provided with electrical conduction properties, are biodegradable.

They also set themselves the aim that said nanowires can be used equally well at a nanoscopic, microscopic and macroscopic scale.

They also set themselves the aim that these nanowires can be easily manufactured at an industrial scale and at a cost such that they can find applications in very numerous fields.

In particular, they set themselves the aim that these nanowires can be manufactured by conventional methods.

DESCRIPTION OF THE INVENTION

These aims and yet others are attained by the invention which proposes, firstly, an electroconducting nanowire, which comprises an amyloid fibre which results from the self-assembling of peptides comprising a prion domain or a derivative of this domain and which is functionalized by electron transporting peptides, each comprising one or more amino acids bound to one or more atoms of iron.

In the foregoing and hereafter, "nanowire" is taken to mean a wire whose thickness is comprised between 1 and 100 nanometers but whose length may, for its part, extend up to 10 micrometers.

It will be recalled that amyloid fibres are fibres that result from the self-assembling of proteins. This self-assembling has the characteristic of self-propagating since the addition of a small quantity of protein in the form of amyloid fibres in a suspension of this same protein accelerates the passage of the quasi-totality of the protein in the form of amyloid fibres.

Amyloid fibres have a characteristic inter-molecular β sheet structure. They show a coloration to Congo red, associated with a birefringence to polarised light (Sipe and Cohen, *Journal of Structural Biology* 2000, 130(2-3), pages 88-98, [2]), and cause a sharp increase in the fluorescence emitted by thioflavin-T at the wavelength of 480 nm (Sabate et al., *Journal of Structural Biology* 2008, 162(3), pages 387-396, [3]). They also have an X-ray diffraction profile which is characteristic of a beta-cross structure.

Amyloid fibres were firstly detected in protein deposits associated with neurodegenerative diseases such as Alzheimer's and Parkinson's diseases. These deposits are the consequence of incorrect folding, with loss of biological activity, of the proteins concerned. This phenomenon is correlated with a destabilisation of the native structure of said proteins by a mutation or by a post-translational modification (proteolysis, phosphorylation, etc.) due to a stress. Amyloid fibres have been the subject of a great number of studies intended to understand their mechanisms of formation in cellular media and their modes of propagation.

Within the scope of these works, a new class of proteins has been discovered, namely proteins with prion domain (Baxa et al., *Advances in Protein Chemistry* 2006, 73, pages 125-180, [4]). These proteins were firstly highlighted in yeasts then in fungi but an increasing number of works suggest that they could also be present in human beings.

Prion domains form fibres that have the main structural characteristics of amyloid fibres: β sheets, fixation of specific markers, etc. These fibres are also known under the name of amyloid fibres.

However, in the case of proteins with prion domain, the formation of amyloid fibres is not due to an incorrect folding of said proteins but forms an integral part of their biological activity and intervenes in physiological conditions and, in particular, at neutral pH. It enables in general the regulation of the function of another domain of the proteins. The structuring of prion domains in amyloid fibres corresponds to the formation of the native structure of these proteins in the same way, for example, that collagen spontaneously forms fibres structured into helices.

In the case of proteins with prion domain, it is thus possible to determine a structure at the atomic scale of the prion domain within the amyloid fibres, which is not the case when the formation of the amyloid fibres is associated with an incorrect folding of the proteins as in the aforementioned neurodegenerative diseases.

In the foregoing and hereafter, "peptide comprising a prion domain or a derivative of this domain" is taken to mean a peptide which comprises the sequence of amino acids of a prion domain or a sequence of amino acids which derives from the sequence of amino acids of a prion domain by one or more modifications of the type addition(s), insertion(s), deletion(s) and/or substitution(s) of one or more amino acid residues, so long as this or these modifications do not alter the capacity of said sequence to form amyloid fibres. The derivatives can also result from one or more post-translational modifications and/or chemical modifications such as an acetylation, a glycosylation, an amidation, an acylation, a methylation as long as this or these modifications do not alter the capacity of said sequence to form amyloid fibres.

The envisaged additions and deletions may concern the C-terminal part and/or the N-terminal part of the sequence of amino acids of the prion domain. These additions can in particular consist of the addition of a short peptide sequence such as a sequence composed of six histidine residues, useful for the purification of the peptide if this is obtained by genetic recombination methods. Like insertions, the envisaged deletions can also concern one or more amino acid residues situated within the sequence of amino acids.

The envisaged substitutions may be substitutions between equivalent amino acids, in other words between amino acids that have similar chemical or physical properties (size, charge or polarity). Nevertheless, they may also be substitutions between non-equivalent amino acids, in other words between amino acids not having structural homology, as long as, as indicated previously, these substitutions do not affect the capacity of the sequence to form amyloid fibres.

Furthermore, these substitutions can just as easily be carried out with amino acids of the genetic code, natural but rare amino acids such as hydroxyproline, hydroxylysine, allohydroxylysine, N-methylglycine or N-ethylglycine, as with synthetic amino acids such as ornithine, norleucine, norvaline or cyclohexylalanine.

Within the scope of the present invention, a derivative of a prion domain comprises, generally speaking, a sequence of amino acids that has at least 25%, preferably at least 50%, better still at least 75% and, in a particularly preferred manner, at least 95% identity with the sequence of amino acids of the prion domain from which it is derived, and has a capacity to form amyloid fibres.

In the foregoing and hereafter, the phrase "which is functionalized by electron transporting peptides" means that the amyloid fibre must be seen as constituting the framework or the skeleton of the electroconducting nanowire and that the electron transporting peptides must be seen as nodules that are fixed on this framework by covalent bonds.

The phrase "each comprising amino acids bound to one or more atoms of iron" means, for its part, that each electron transporting peptide comprises amino acids which are bound directly to one or more atoms of iron by coordination bonds established between these amino acids and this or these atoms of iron.

In the electroconducting nanowire according to the invention, each peptide comprising a prion domain or a derivative of this domain is, preferably, functionalized by—and thus bound to—an electron transporting peptide, such that the electron transporting peptides can be regularly arranged along the length of the amyloid fibre and that the occurrence of a rupture in the transfer of electrons that takes place along this fibre is thereby avoided. The structure thereby obtained is illustrated schematically in appended FIG. 1, in which each peptide comprising a prion domain or a derivative of this domain is referenced 1, each electron transporting peptide is referenced 2 whereas the amyloid fibre resulting from the self-assembling of the peptides comprising a prion domain or a derivative of this domain is referenced 3.

According to the invention, the electron transporting peptides are advantageously peptides derived from a protein with iron-sulphur centre.

In the foregoing and hereafter, "peptide derived from a protein with iron-sulphur centre" is taken to mean a peptide in which the sequence of amino acids comprises the sequence of amino acids of a protein with iron-sulphur centre, or a sequence of amino acids which derives from this sequence by one or more modifications of the type addition(s), insertion(s), post-translational and/or chemical modification(s), deletion(s) and/or substitution(s) of one or more amino acid residues, as long as this or these modifications do not alter the capacity of said sequence to transport electrons.

The envisaged additions, insertions, post-translational and/or chemical modifications, deletions and substitutions are of the same type as those evoked previously.

It will be recalled that proteins with iron-sulphur centre are proteins that bind a cofactor composed of an atom of iron or atoms of iron and sulphur, through the intermediary of sulphur atoms of cysteine residues, nitrogen atoms of histidine residues, oxygen atoms of serine residues or aspartic acid residues.

Thus, proteins with an iron-sulphur centre must not be confused with hemoproteins or proteins with heme, such as cytochrome C, which also bind a metal cofactor but in which said cofactor is composed of a non-protein nucleus, of the porphyrin type, to which is coordinated an atom of iron.

Proteins with iron-sulphur centre are present in all living beings and serve for different functions, of which the transfer of electrons (Blondin and Girerd, *Chemical Reviews* 1990, 90(8), pages 1359-1376, [5]). Their oxidoreduction potential ranges typically from −500 mV to more than 500 mV.

The iron-sulphur centres the most often encountered in living beings are the centres [Fe], [2Fe-2S], [3Fe-4S] and [4Fe-4S] hereafter:

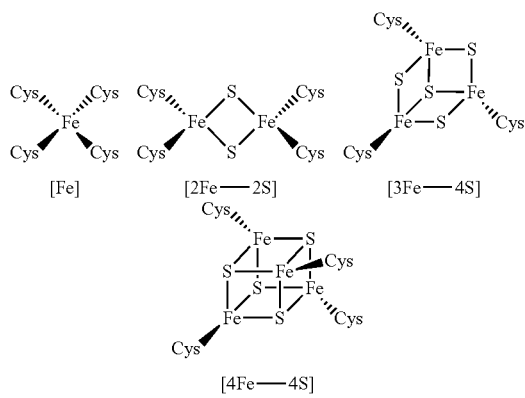

The centres [Fe] are usually encountered in proteins of low molecular weight (in other words at the most 6 kDa), which are known as rubredoxins and which are present in anaerobic bacteria such as the bacteria of the genus *Methanococcus* or *Desulfovibrio*, whereas the centres [2Fe-2S], [3Fe-4S] and [4Fe-4S] are usually encountered in proteins of higher molecular weight (typically from 6 to 15 kDa) such as ferredoxins and hydrogenases, and which are, for their part, present in anaerobic bacteria such as *Clostridium pasteurianum* but also in algae, higher plants and in vertebrates (mammals in particular).

Also, the protein from which are derived the electron transporting peptides is, preferably, selected from rubredoxins, ferredoxins and hydrogenases.

Among these, preference is given to rubredoxins and, in particular, to the rubredoxin of *Methanococcus voltae*, which has the following sequence of amino acids:

(SEQ ID NO: 1)
MAIWQCTVCGYKYDEDKEKKKFEDLPADCKCPVCGAKKEMFKKL.

This rubredoxin has, in fact, the advantage of being of small size (MW=5 kilodaltons) and of having an isoelectric potential close to 7. This overall neutrality makes it possible to limit the repulsive forces between the electron transporting peptides on the amyloid fibre and thereby prevent the iron centres of said peptides moving away from each other.

It has, in addition, a very great stability even in denaturing conditions for the quasi-totality of the proteins (8 moles/L urea or pH<3). This is particularly interesting in the case where the electroconducting nanowires according to the invention are prepared by expression, in a host cell, of chimeric proteins each comprising a peptide comprising a prion domain or a derivative of this domain, and a peptide derived from this rubredoxin, then formation of amyloid fibres by self-assembling of peptides comprising a prion domain or a derivative of this domain that these chimeric proteins comprise.

In fact, thanks to this stability, it is possible to purify the chimeric proteins thereby expressed in conditions in which the peptides derived from the rubredoxin are functional whereas the peptides comprising a prion domain or a derivative of this domain are denatured and then induce the formation of amyloid fibres by placing said chimeric proteins in a re-naturing environment for the peptides derived from the rubredoxin.

One thereby does away with a step of re-naturation of peptides derived from the rubredoxin and reconstitution of its iron-sulphur centre, knowing that this step is generally complicated to carry out and necessitates having available very specific equipment such as glove boxes. A non-negligible benefit ensues in the perspective of an industrial production of nanowires.

Electron transporting peptides derived from the rubredoxin of *Methanococcus voltae* comprise, preferably, the sequence of amino acids SEQ ID NO: 1 or a sequence of amino acids which derives from this sequence by one or more modifications of the type addition(s), insertion(s), post-translational and/or chemical modification(s), deletion(s) and/or substitution(s) of one or more amino acid residues, as long as this or these modifications do not concern the cysteine residues involved in the iron-sulphur centre of the rubredoxin, in other words the cysteine residues situated in positions 6, 9, 31 and 34 of the sequence ID NO: 1, and, consequently, do not affect the functionality of said centre.

Typically, the peptides that comprise a sequence of amino acids thereby derived from the sequence ID NO: 1 comprise a sequence of amino acids that has at least 25%, preferably at least 50% and, better still, at least 75% identity with said sequence.

In this respect, it will be recalled that the identity of a sequence compared to a reference sequence is assessed as a function of the percentage residues of amino acids that are identical, when the two sequences are aligned, so as to obtain the maximum correspondence between them. This percentage is obtained after implementation of the best alignment (optimum alignment) between the two sequences. Those skilled in the art know different techniques that make it possible to obtain such a percentage identity and involving homology algorithms or computer programmes such as the BLAST programme.

The percentage identity is statistical and the differences between the two sequences are randomly distributed along said sequences. This definition applies by analogy to nucleotide sequences.

Peptides that comprise a sequence of amino acids derived from the sequence SEQ ID NO: 1 are, for example, peptides that comprise:

the following sequence of amino acids:

(SEQ ID NO: 2)
MAIWQCTVCGYKYDEDKEKKKFEDLPADYKCPVCGAKKEMFKKL, which differs from the sequence of amino acids SEQ ID NO: 1 in that the cysteine residue situated in position of this sequence has been replaced by a tyrosine residue (the non-matching cysteine residues being, in fact, known to have a destabilising effect on the iron-sulphur centres); or the following sequence of amino acids:

(SEQ ID NO: 3)
AIWQCTVCGYKYDEDKEKKKFEDLPADCKCPVCGAKKEMFKKL, which differs from the sequence of amino acids SEQ ID NO: 1 in that the N-terminal methionine residue of this sequence has been deleted; or the following sequence of amino acids:

(SEQ ID NO: 4)
IWQCTVCGYKYDEDKEKKKFEDLPADCKCPVCGAKKEMFKKL, which differs from the sequence of amino acids SEQ ID NO: 3 in that the N-terminal alanine residue of this sequence has been deleted; or the following sequence of amino acids:

(SEQ ID NO: 5)
MAIWQCTVCGYKYDEDKEKKKFEDLPADCKCPVCGAKKEMFKK, which differs from the sequence of amino acids SEQ ID NO: 1 in that the C-terminal leucine residue of this sequence has been deleted; or the following sequence of amino acids:

(SEQ ID NO: 6)
MAIWQCTVCGYKYDEDKEKKKFEDLPADYKCPVCGAKKEMFKKS, which differs from the sequence of amino acids SEQ ID NO: 2 in that the C-terminal leucine residue of this sequence has been replaced by a serine residue; or the following sequence of amino acids:

(SEQ ID NO: 7)
AIWQCTVCGYKYDEDKEKKKFEDLPADYKCPVCGAKKEMFKKS, which differs from the sequence of amino acids SEQ ID NO: 1 at one and the same time in that the N-terminal methionine residue has been deleted, the cysteine residue situated in position 29 has been replaced by a tyrosine residue, and in that the C-terminal leucine residue has been replaced by a serine residue.

According to the invention, the peptides comprising a prion domain or a derivative of this domain are, preferably, derived from the Het-s protein, which is a prior protein of the filamentous fungus *Podospora anserina*.

This protein is constituted of 289 residues of amino acids and is involved in the function of self and non-self recognition (Dos Reis et al., *Journal of Biological Chemistry* 2002, 277(8), pages 5703-5706, [6]; Balguerie et al., *Embo Journal* 2003, 22(9), pages 2071-2081, [7]; Maddelein et al., 2002, *Proceedings of the National Academy of Sciences of the United States of America*, 2002, 99(11), pages 7402-7407 [8]).

The residues 1 to 217 contain the actual recognition function whereas the residues 218 to 289 are responsible for the formation of amyloid fibres which are the support of the recognition function.

Also, the peptides comprising a prion domain or a derivative of this domain comprise, preferably, the following sequence of amino acids:

(SEQ ID NO: 8)
KIDAIVGRNSAKDIRTEERARVQLGNVVTAAALHGGIRISDQTTNSVET
VVGKGESRVLIGNEYGGKGFWDN, which corresponds to the residues 218 to 289 of the Het-s protein, or a sequence of amino acids which derives from this sequence by one or more modifications of the type addition(s), insertion(s), post-translational and/or chemical modification(s), deletion(s) and/or substitution(s) of one or more amino acid residues, as long as this or these modification(s) do not concern the amino acid residues involved in the stability of this sequence.

In this particular case, the amino acid residues involved in the stability of the sequence of amino acids SEQ ID NO: 8 are the following:

residues 9 to 17 of the sequence SEQ ID NO: 8 corresponding to residues 226 to 234 of the Het-s protein;
residues 20 to 27 of the sequence SEQ ID NO: 8 corresponding to residues 237 to 244 of the Het-s protein;
residues 45 to 54 of the sequence SEQ ID NO: 8 corresponding to residues 262 to 271 of the Het-s protein;
residues 56 to 65 of the sequence SEQ ID NO: 8 corresponding to residues 273 to 282 of the Het-s protein;
residues 9 and 45 of the sequence SEQ ID NO: 8 corresponding to residues 226 and 262 of the Het- protein;
residues 12 and 48 of the sequence SEQ ID NO: 8 corresponding to residues 229 and 265 of the Het-s protein;
residues 17 and 53 of the sequence SEQ ID NO: 8 corresponding to residues 234 and 270 of the Het-s protein;
residues 19 and 55 of the sequence SEQ ID NO: 8 corresponding to residues 236 and 272 of the Het-s protein; and residues 11, 14, 20, 22, 24, 47, 50, 58 and 60 of the sequence SEQ ID NO: 8 corresponding to residues 228, 231, 237, 239, 241, 264, 267, 275 and 277 of the Het-s protein.

Here also, the peptides that comprise a sequence of amino acids thereby derived from the sequence of amino acids SEQ ID NO: 8 comprise a sequence of amino acids which has at least 25%, preferably at least 50%, better still at least 75% and, in a particularly preferred manner, at least 95% identity with said sequence.

Peptides that comprise a sequence of amino acids derived from the sequence SEQ ID NO: 8 are, for example, the peptide which comprises the following sequence of amino acids:

(SEQ ID NO: 13)
MEIDAIVGRNSAKDIRTEERARVQLGNVVTAAALHGGIRISDQTTNSVE

TVVGKGESRVLIGNEYGGKGFWDN, which differs from the sequence of amino acids SEQ ID NO: 8 in that the N-terminal lysine residue of this sequence has been replaced by a glutamic acid residue and in that a methionine residue has been added at the N-terminal, and the peptides that comprise a sequence of amino acids that derives from SEQ ID NO: 13 by one or more modifications of the type addition(s), insertion(s), post-translational and/or chemical modification(s), deletion(s) and/or substitution(s) of one or more amino acid residues.

In a variant, the peptides comprising a prion domain or a derivative of this domain may also be derived from a prion protein other than Het-s such as, for example, a Sup35 or Ure2p protein, which are two prion proteins of yeasts for which the formation of amyloid fibres is necessary for their function.

In a particularly preferred manner, the electroconducting nanowire according to the invention is constituted of an amyloid fibre which results from the self-assembling of peptides comprising the aforementioned sequence of amino acids SEQ ID NO: 13, each peptide of said assemblage being functionalized by—and thus bound to—a peptide comprising the aforementioned sequence of amino acids SEQ ID NO: 6.

Also in a particularly preferred manner, the electroconducting nanowire according to the invention has a thickness of 5 to 10 nm and, better still, of the order of 8 nm and a length ranging from 100 nm to 10 µm and, better still, from 200 nm to 2 µm.

The electroconducting nanowire according to the invention may be manufactured by methods consisting in grafting electron transporting peptides, each comprising one or more amino acids bound to one or more atoms of iron, onto an amyloid fibre.

Nevertheless, in the case where each peptide comprising a prion domain or a derivative of this domain that comprises the nanowire is functionalized by an electron transporting peptide, said nanowire may advantageously be manufactured by methods conventionally employed for the production of recombinant proteins and, in particular, by a method comprising:

a) transforming a host cell using an expression vector comprising a polynucleotide which encodes a chimeric protein comprising a peptide comprising a prion domain or a derivative of this domain and an electron transporting peptide comprising one or more amino acids bound to one or more atoms of iron;

b) culturing the host cell in a culture medium;

c) recovering from the host cell, the chimeric proteins expressed by the polynucleotide; and d) forming the nanowire by assembling the peptides derived from the protein with prion domain which the chimeric proteins thereby recovered comprise.

Thus, the subject matter of the invention is also a method for manufacturing an electroconducting nanowire as defined previously, which comprises the aforementioned steps a) to d).

In accordance with what has been stated beforehand, the electron transporting peptide, which is present in the chimeric protein, is advantageously a peptide derived from a protein with iron-sulphur centre and, better still, a peptide that is derived from a protein selected from rubredoxins, ferredoxins and hydrogenases.

In which case, it is preferred that this peptide is derived from a rubredoxin and, preferably, from the rubredoxin of *Methanococcus voltae* and, in particular, that it comprises the aforementioned sequence of amino acids SEQ ID NO: 1 or a sequence of amino acids which derives from this sequence by one or more modifications of the type addition(s), insertion(s), post-translational and/or chemical modification(s), deletion(s) and/or substitution(s) of one or more amino acid residues, as long as this or these modifications do not concern the cysteine residues involved in the iron-sulphur centre of the rubredoxin.

Furthermore, it is preferred that the peptide comprising a prion domain or a derivative of this domain is a peptide derived from the Het-s prion protein of *Podospora anserina* and, in particular, that said peptide comprises the aforementioned sequence of amino acids SEQ ID NO: 13 or a sequence of amino acids which derives from this sequence by one or more modifications of the type addition(s), insertion(s), post-translational and/or chemical modification(s), deletion(s) and/or substitution(s) of one or more amino acid residues, as long as this or these modifications do not concern the amino acid residues involved in the stability of this sequence.

Quite particularly, it is preferred that the chimeric protein comprises a peptide comprising the aforementioned sequence of amino acids SEQ ID NO: 13 and a peptide comprising the aforementioned sequence of amino acids SEQ ID NO: 6.

Thus, for example, said chimeric protein comprises or is constituted of the following sequence of amino acids:

(SEQ ID NO: 9)
MAIWQCTVCGYKYDEDKEKKKFEDLPADYKCPVCGAKKEMFKKSMEIDA

IVGRNSAKDIRTEERARVQLGNVVTAAALHGGIRISDQTTNSVETVVGK

GESRVLIGNEYGGKGFWDN.

Another subject matter of the invention is a chimeric protein as defined previously as well as a polynucleotide which comprises a nucleotide sequence encoding this chimeric protein.

As known per se, this polynucleotide may be equally well a single strand DNA, a double strand DNA or an RNA.

In addition, the subject matter of the invention is an expression vector containing a polynucleotide according to the invention, said expression vector being particularly useful for transforming a host cell and expressing the chimeric protein according to the invention in said cell, as well as a host cell comprising said expression vector.

As known per se, the expression vector according to the invention comprises, apart from the polynucleotide encoding the chimeric protein, one or more elements that enable the expression of this chimeric protein in the host cell.

As examples of such elements, a constitutive or inducible promoter, a transcription initiation signal, a transcription termination signal, a translation initiation sequence, a translation end signal may be cited.

This vector is advantageously selected from plasmids, cosmids, bacteriophages and viruses such as a baculovirus. Such vectors are well known to those skilled in the art and widely described in the literature.

As for the host cell, it may be any uni- or multicellular organism, lower or higher, capable of being transformed by an invention vector according to the invention.

Thus, it may in particular be a yeast, a bacterium such as *Escherichia coli*, a fungus, a plant cell, an insect cell, or even a mammal cell with the exception of a human cell.

Given their remarkable properties, the electroconducting nanowires according to the invention can find very numerous applications.

Thus, for example, in so far as it may be predicted with certainty that the electrical conduction of these nanowires will be modified by interactions with chemical or biological species, said nanowires are likely to be used in sensors earmarked for the detection of chemical or biological species.

In this context, it is in particular possible to envisage a functionalization of the electroconducting nanowires according to the invention by an enzyme, the activity of which produces electrons such as, for example, glucose oxidase or cholesterol esterase, which would then enable the sensors to detect the presence of glucose or cholesterol with a very high sensitivity since the electrons produced by the activity of the enzyme would then be collected by the nanowires.

This type of approach could also be taken advantage of to use the electroconducting nanowires according to the invention in nano-batteries. In fact, the electrons produced by the activity of an enzyme could serve to supply a nano-battery which would then be constituted of electroconducting nanowires according to the invention and, thus, be biodegradable.

In the same way, instead of binding a protein delivering an electron from a substrate, it may be envisaged to bind a photosensitive protein or molecule, delivering an electron following a light excitation. This could thus be used to convert solar energy into electricity.

Furthermore, one of the flaws of conducting polymers being that they are not biodegradable, the nanowires according to the invention are liable to replace these conducting polymers in all their macroscopic uses. Thus, for example, electroconducting nanowires according to the invention could be used for the manufacture of radio-identification systems, also known as RFID (Radio Frequency IDentification) systems, such as radio-labels.

Finally, molecular electronics aiming to implement electron transfer phenomena at the scale of the molecule and, in particular, the unique transfer of electrons, the electroconducting nanowires according to the invention are capable of being used in all molecular electronics applications.

Other characteristics and advantages of the invention will become clear from the description complement that follows and which relates to an example of embodiment of electroconducting nanowires according to the invention as well as an example concerning the characterisation of said nanowires and the highlighting of their properties.

Obviously, this description complement is only given by way of illustration of the invention and does not constitute in any way a limitation.

DETAILED DESCRIPTION OF A PARTICULAR EMBODIMENT

Example 1

Figure 1:
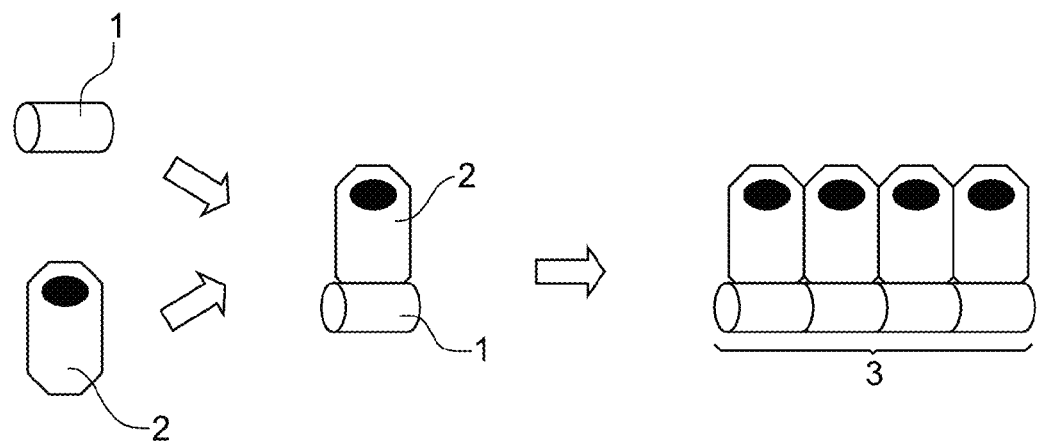
FIG. 1, already commented upon, schematically illustrates a preferred structure of an electroconducting nanowire according to the invention.
Figure 2:
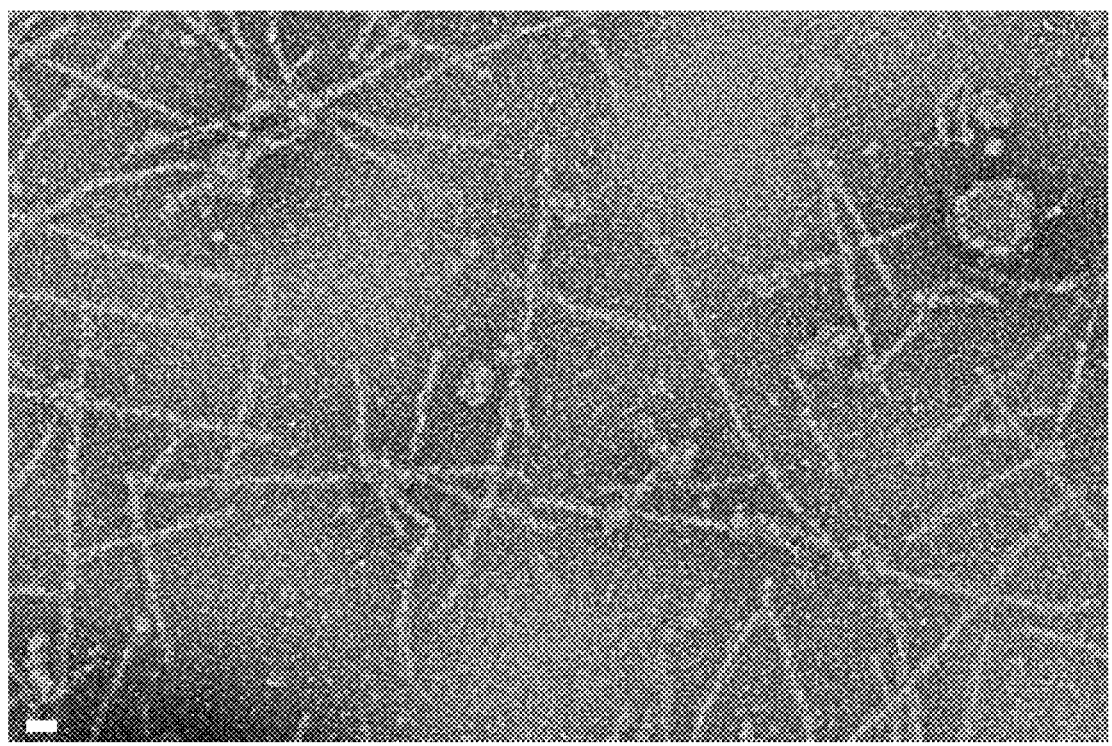
FIG. 2 represents an image taken in transmission electron microscopy by negative coloration of electroconducting nanowires according to the invention.

Formation of Electroconducting Nanowires According to the Invention

Electroconducting nanowires are formed by expression, in cells of *Escherichia coli*, of chimeric proteins each comprising the aforementioned sequence of amino acids SEQ ID NO: 9, to which has been added, on the side of the C-terminal asparagine residue of this sequence, a tag composed of 6 histidine residues intended to enable the purification by IMAC (Immobilized Metal Affinity Chromatography), and, more specifically on a nickel column, of the chimeric proteins thereby expressed.

Chimeric proteins thus have the following sequence of amino acids:

```
                                    (sequence ID NO: 10)
MAIWQCTVCGYKYDEDKEKKKFEDLPADYKCPVCGAKKEMFKKSMEIDA

IVGRNSAKDIRTEERARVQLGNVVTAAALHGGIRISDQTTNSVETVVGK

GESRVLIGNEYGGKGFWDNHHHHHH.
```

To do this, the nucleotide sequence encoding for the peptide with prion domain:

```
                                    (sequence ID NO: 11)
ATGGAGATCGACGCGATTGTGGGAAGGAATTCCGCCAAGGATATCGAAA

CAGAGGAACGTGCAAGGGTCCAGCTCGGCAATGTTGTCACTGCGGCAGC

CCTACATGGTGGGATCCGTATCAGCGACCAGACAACCAACTCGGTAGAG
```

-continued

ACGGTTGTGGGGAAGGGCGAGTCTAGGGTCCTTATTGGAAATGAGTACG

GAGGTAAGGGGTTCTGGGATAATCACCATCACCATCATCACTAA is extracted from the genome of the original organism by PCR, and introduced into the expression vector pt7-7 between the NcoI and HindIII restriction sites.

Then, the sequence encoding for the electroconducting peptide:

(sequence ID NO: 12)
ATGGCGATCTGGCAGTGTACCGTTTGCGGTTACAAATACGATGAAGATA

AAGAAAAGAAAAAATTTGAAGACCTGCCGGCGGATTACAAATGTCCGGT

TTGCGGTGCGAAAAAAGAAATGTTTAAGAAATCC is obtained by chemical synthesis route and introduced into the same expression vector pt7-7 between the NdeI and NcoI restriction sites.

The introduction of sequences into an expression vector takes place via the aforementioned restriction sites. The restriction sites have the particularity of having a sequence known as palindromic (the complementary strand inverted at the same sequence) of 4 to 8 nucleotides. This sequence may be cleaved specifically by the restriction enzyme of the same name and ligated (if there is complementarity of sequences) by a ligase. T4 DNA ligase has been used in the present example.

The expression vector thereby modified is introduced in its turn into cells of *Escherichia coli* BL21(DE3)PlysS.

The introduction of vector into the cells is what is known as a transformation. It is carried out in the following manner:
 addition of the plasmid into the extra-cellular medium;
 incubation of a duration of 30 to 60 minutes at 4° C.;
 thermal shock of a duration of 30 seconds to 2 minutes at 42° C.;
 15 minutes at 4° C.;
 spreading on LB agar plates to select the bacteria resistant to the antibiotic (in other words having integrated the expression vector).

The cells of *Escherichia coli* thereby transformed are then cultivated in a 50 µmol/L iron enriched minimal medium until the optical density (DO) attains a value of 0.7. The expression of the proteins is then induced by adding 1 mM of imidazole into the medium and the bacteria are incubated for 4 additional hours.

After which:
 the culture medium is centrifuged at 4 000 rcf;
 the bacterial pellets are re-suspended in a tris buffer, pH 8, containing 8 mol/L of urea to inhibit the formation of amyloid fibres by the expressed chimeric proteins;
 the cells are lysed by sonication;
 the cellular lysates are centrifuged at 40 000 rcf and filtered at 0.45 µm to eliminate the non-soluble part thereof;
 the soluble part of the cellular lysates is loaded onto a nickel column previously equilibrated with buffer A (tris-HCl: 10 mmol/L; urea: 8 mol/L; pH: 8);
 the column is washed with buffer A then with buffer A to which has been added 25 mol/L of imidazole;
 the column is eluted with buffer A to which has been added 300 mmol/L of imidazole; and
 the buffer wherein are found the chimeric proteins thereby recovered is dialysed against 1% acetic acid (pH 2.7) so as to be able to conserve these chimeric proteins without them forming amyloid fibres.

In these conditions, it is possible to recover 8 mg of chimeric proteins from one liter of bacteria culture in an Erlenmeyer flask.

The formation of the amyloid fibres is then triggered by dialysis of acetic acid against water.

Example 2

Figure 3:
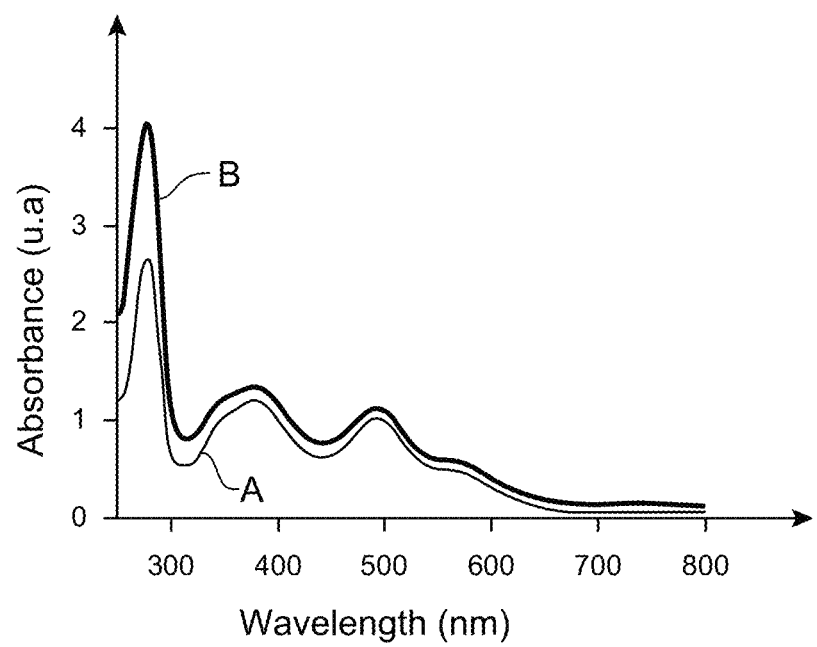
FIG. 3 represents the UV-visible absorbance spectrum (expressed in arbitrary units) of the rubredoxin of *Methanococcus voltae* (spectrum A) and that of electroconducting nanowires according to the invention, obtained by expression of the chimeric protein comprising the aforementioned sequence of amino acids SEQ ID NO: 5 in cells of *Escherichia coli* (spectrum B).

Characterisation and Properties of Electroconducting Nanowires According to the Invention 2.1. Fibrillar Structure of the Nanowires FIG. 3 shows an image taken in transmission electron microscopy by negative coloration with uranyl salt of the nanowires obtained in example 1 and on which the scale, which is represented by the rectangle situated in the bottom left hand corner of this image, corresponds to 20 nm.

This figure shows that the nanowires have, as expected, a fibrillar structure and that they have substantially a thickness of 8 nm for a length ranging from 200 nm to 2 µm.

2.2. Electroconducting Properties of Nanowires

In order that the nanowires obtained in example 1 above can conduct electrons on either side of the amyloid fibre which constitutes them, it is important that the peptide sequences derived from the rubredoxin of *Methanococcus voltae*, which functionalize this amyloid fibre, are correctly folded on their iron-sulphur centre.

The rubredoxin of *Methanococcus voltae* has typical UV-visible absorbance rays at 360, 380, 490, 570 and 750 nm.

Also, to verify that the peptide sequences functionalizing the amyloid fibre of the nanowires are correctly folded on their iron-sulphur centre and, consequently, functional, the absorbance of these nanowires is thus measured at the aforementioned wavelengths.

To do this, a UV-visible spectroscope is used in scanning mode between 800 and 250 nm. The sample is placed in a quartz chamber of optical path equal to 1 cm, traversed by the beam of the spectroscope which thus measures the absorbance of the protein solution at all wavelengths in the scanning range.

The results are shown in FIG. 3 in which curve A represents the UV-visible absorbance spectrum of the rubredoxin of *Methanococcus voltae* whereas curve B represents the UV-visible absorbance spectrum of the nanowires.

This figure shows that the UV-visible absorbance rays of the nanowires are identical to those of the rubredoxin of *Methanococcus voltae* and the nanowires, which signifies that the peptide sequences functionalizing the amyloid fibre of the nanowires are correctly folded on their iron-sulphur centre and functional.

Furthermore, the capacity of an object to conduct electrons, wherein said capacity is based on oxidoreduction reactions, may be assessed by cyclic voltammetry.

The principle of this technique is to apply a potential, which is made to vary in a cyclical manner, to a solution in which is found the object and to measure the current supplied or accepted by the electron donor or acceptor chemical species that said objet comprises.

This provides information on the redox potential of these chemical species and on their diffusive character. In fact, the transfer of electrons from a chemical species to the working electrode depends on the capacity of this species to diffuse on the surface of this electrode.

According to the scanning speed of the potential applied, this diffusion is different and the number of electrons transferred is different. On the other hand, if the chemical species is adsorbed on the working electrode, it does not diffuse.

A law makes it possible to link the electronic current supplied by the electron donor chemical species to the scanning speed of the potential through the intermediary of the coefficient of diffusion of said species.

Figure 4:
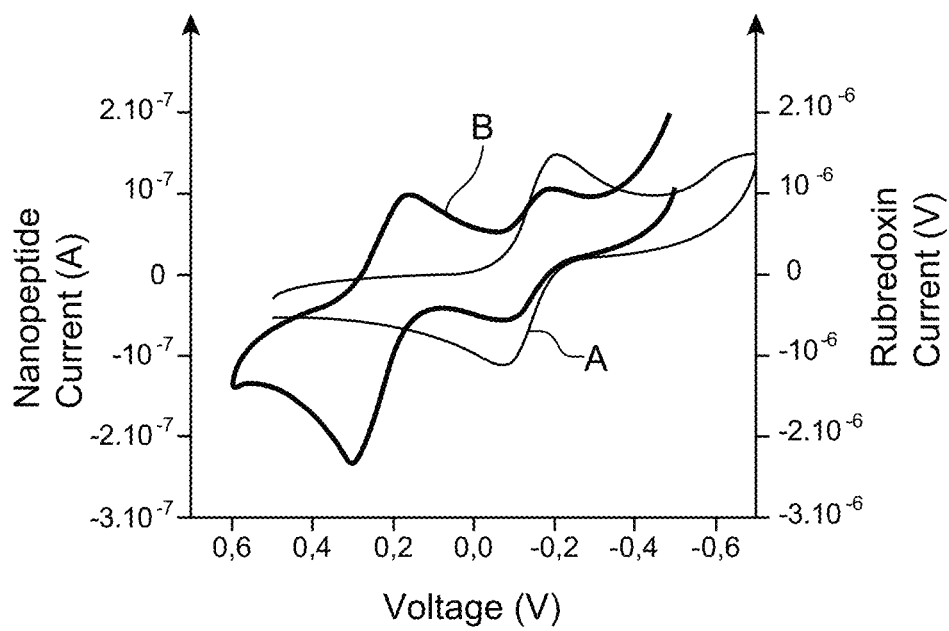
FIG. 4 represents the voltammograms recorded in cyclic voltammetry for the rubredoxin of *Methanococcus voltae* (voltammogram A) and for nanowires according to the invention, obtained by expression of chimeric proteins each comprising the aforementioned sequence of amino acids SEQ ID NO: 5 in *Escherichia coli* cells (voltammogram B).

This being made clear, when the rubredoxin of *Methanococcus voltae* is subjected to a cyclic voltammetry test (vitreous carbon working electrode, Ag/AgCl reference electrode, platinum counter-electrode, 340 μmol/L rubredoxin solution, 100 mM NaCl, scanning speed of 30 mV/s), the voltammogram A of FIG. 4 is obtained. The rubredoxin has a potential oxidoreduction of −100 mV and a coefficient of diffusion of $1.5.10^{-10}$ m$^2$/s.

When the nanowires obtained in example 1 are subjected to a cyclic voltammetry test in the same conditions, the voltammogram B shown in FIG. 4 is obtained. It may be observed that these nanowires are adsorbed on the surface of the working electrode. Consequently, the electrons can no longer be transported to the working electrode by diffusion of the sequences derived from the rubredoxin of *Methanococcus voltae*.

Figure 5:
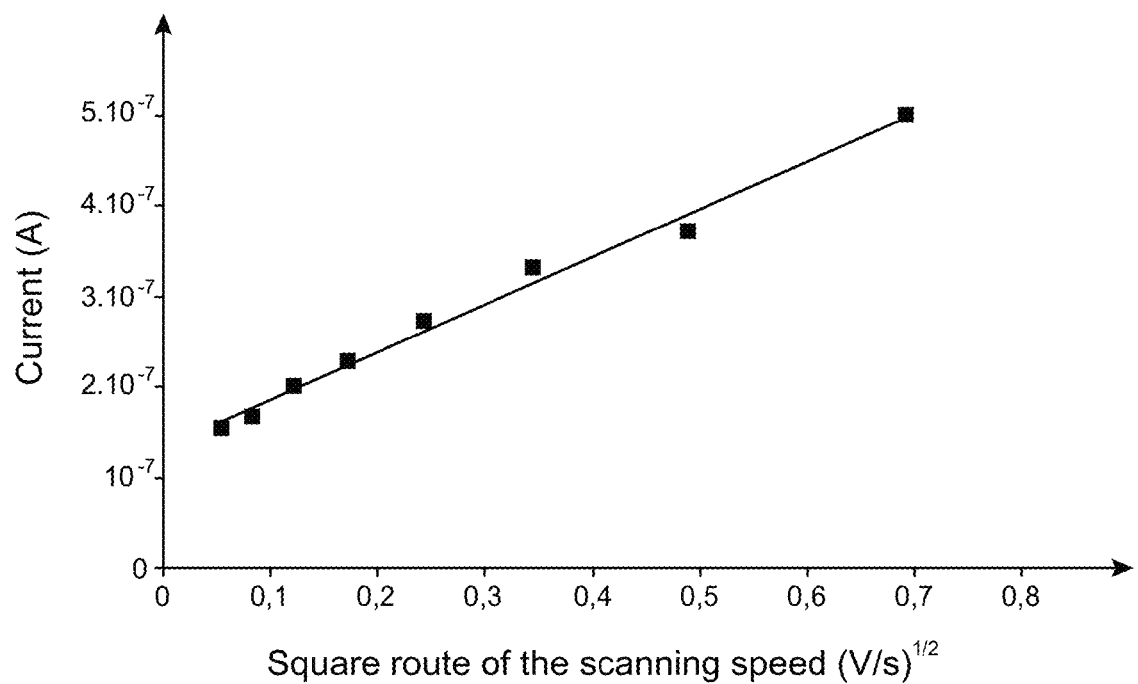
FIG. 5 represents the variations in reduction of peak current (expressed in amperes) as a function of the square root of the scanning speed (expressed in $(V/s)^{1/2}$), as recorded in cyclic voltammetry for nanowires according to the invention, obtained by expression of chimeric proteins each comprising the aforementioned sequence of amino acids SEQ ID NO: 5 in cells of *Escherichia coli*.

Yet, as shown in FIG. 4, a second redox couple is seen to appear at around +250 mV, the reduction peak of which, as shown in FIG. 5, retains a diffusive character when the scanning speed is made to vary. The coefficient of diffusion cannot be calculated precisely because the concentration of nanowires is unknown in the present test. However, it is known that it is at least two orders of magnitude lower than that of the rubredoxin alone. The only explanation for these different phenomena is that the electrons diffuse along the nanowires, which signifies that said nanowires can transport an electric current.

REFERENCES CITED

[1] Jones and Grainger, *Advanced Drug Delivery Reviews* 2009, 61(6), pages 438-456
[2] Sipe and Cohen, *Journal of Structural Biology* 2000, 130(2-3), pages 88-98
[3] Sabate et al., *Journal of Structural Biology* 2008, 162(3), pages 387-396
[4] Baxa et al., *Advances in Protein Chemistry* 2006, 73, pages 125-180
[5] Blondin and Girerd, *Chemical Reviews* 1990, 90(8), pages 1359-1376
[6] Dos Reis et al. 2002, *Journal of Biological Chemistry*, 277(8), pages 5703-5706
[7] Balguerie et al. 2003, *Embo Journal*, 22(9), pages 2071-2081
[8] Maddelein et al., 2002, *Proceedings of the National Academy of Sciences of the United States of America*, 2002, 99(11), pages 7402-7407

---

The invention claimed is:

1. An electroconducting nanowire, comprising an amyloid fibre which results from a self-assembling of first peptides comprising a prion domain or a derivative of the prion domain, the derivative being capable of forming amyloid fibres, each first peptide comprising the following sequence of amino acids:

(SEQ ID NO: 8)
KIDAIVGRNSAKDIRTEERARVQLGNVVTAAALHGGIRISDQTTNSVETV
VGKGERSRVLIGNEYGGKGFWDN, or a sequence of amino acids having at least 75% identity with SEQ ID NO: 8, the amyloid fibre being linked by covalent bonds to second peptides, the second peptides being electron transporting peptides, each electron transporting peptide comprising amino acids bound to one or more atoms of iron and comprising a sequence of amino-acids of a protein with an iron-sulphur centre, or a sequence of amino-acids having at least 75% identity with the sequence of amino-acids of the protein with the iron-sulphur centre, the protein with the iron-sulphur centre being a rubredoxine, a ferredoxin or a hydrogenase.

2. The electroconducting nanowire of claim 1, wherein each first peptide is linked by one covalent bond to a second peptide.

3. The electroconducting nanowire of claim 1, wherein the protein with the iron-sulphur centre is a rubredoxin.

4. The electroconducting nanowire of claim 3, wherein the rubredoxin is a rubredoxin of *Methanococcus voltae*.

5. The electroconducting nanowire of claim 4, wherein each second peptide comprises the following sequence of amino acids:

(SEQ ID NO: 1)
MAIWQCTVCGYKYDEDKEKKKFEDLPADCKCPVCGAKKEMFKKL, or a sequence of amino acids having at least 75% identity with SEQ ID NO: 1.

6. The electroconducting nanowire of claim 1, wherein the first peptides comprise the following sequence of amino acids:

(SEQ ID NO: 13)
MEIDAIVGRNSAKDIRTEERARVQLGNVVTAAALHGGIRISDQTTNSVE

TVVGKGESRVLIGNEYGGKGFWDN.

7. The electroconducting nanowire of claim 1, which is constituted of the amyloid fibre which results from the self-assembling of first peptides each having the following sequence of amino acids:

(SEQ ID NO: 13)
MEIDAIVGRNSAKDIRTEERARVQLGNVVTAAALHGGIRISDQTTNSVE

TVVGKGESRVLIGNEYGGKGFWDN, each first peptide being linked by a covalent bond to a second peptide having the following sequence of amino acids:

(SEQ ID NO: 6)
MAIWQCTVCGYKYDEDKEKKKFEDLPADYKCPVCGAKKEMFKKS.

* * * * *

SEQUENCE LISTING

```
<160> NUMBER OF SEQ ID NOS: 13

<210> SEQ ID NO 1
<211> LENGTH: 44
<212> TYPE: PRT
<213> ORGANISM: Methanococcus voltae
<220> FEATURE:
<221> NAME/KEY: PEPTIDE
<222> LOCATION: (1)..(44)
<223> OTHER INFORMATION: Rubredoxin

<400> SEQUENCE: 1

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Cys Lys Cys Pro
            20                  25                  30

Val Cys Gly Ala Lys Lys Glu Met Phe Lys Lys Leu
        35                  40

<210> SEQ ID NO 2
<211> LENGTH: 44
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(44)
<223> OTHER INFORMATION: Sequence derived from the sequence SEQ ID NO: 1

<400> SEQUENCE: 2

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Tyr Lys Cys Pro
            20                  25                  30
```

Val Cys Gly Ala Lys Lys Glu Met Phe Lys Lys Leu
          35                  40

<210> SEQ ID NO 3
<211> LENGTH: 43
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(43)
<223> OTHER INFORMATION: Sequence derived from the sequence SEQ ID NO: 1

<400> SEQUENCE: 3

Ala Ile Trp Gln Cys Thr Val Cys Gly Tyr Lys Tyr Asp Glu Asp Lys
1               5                   10                  15

Glu Lys Lys Lys Phe Glu Asp Leu Pro Ala Asp Cys Lys Cys Pro Val
            20                  25                  30

Cys Gly Ala Lys Lys Glu Met Phe Lys Lys Leu
        35                  40

<210> SEQ ID NO 4
<211> LENGTH: 42
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(42)
<223> OTHER INFORMATION: Sequence derived from the sequence SEQ ID NO: 1

<400> SEQUENCE: 4

Ile Trp Gln Cys Thr Val Cys Gly Tyr Lys Tyr Asp Glu Asp Lys Glu
1               5                   10                  15

Lys Lys Lys Phe Glu Asp Leu Pro Ala Asp Cys Lys Cys Pro Val Cys
            20                  25                  30

Gly Ala Lys Lys Glu Met Phe Lys Lys Leu
        35                  40

<210> SEQ ID NO 5
<211> LENGTH: 43
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(43)
<223> OTHER INFORMATION: Sequence derived from the sequence SEQ ID NO: 1

<400> SEQUENCE: 5

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Cys Lys Cys Pro
            20                  25                  30

Val Cys Gly Ala Lys Lys Glu Met Phe Lys Lys
        35                  40

<210> SEQ ID NO 6
<211> LENGTH: 44
<212> TYPE: PRT
<213> ORGANISM: Artificial Sequence
<220> FEATURE:
<223> OTHER INFORMATION: Synthesized sequence

```
<220> FEATURE:
<221> NAME/KEY: PEPTIDE
<222> LOCATION: (1)..(44)
<223> OTHER INFORMATION: Sequence derived from sequence SEQ ID NO: 1

<400> SEQUENCE: 6

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Tyr Lys Cys Pro
                20                  25                  30

Val Cys Gly Ala Lys Lys Glu Met Phe Lys Lys Ser
            35                  40

<210> SEQ ID NO 7
<211> LENGTH: 43
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(43)
<223> OTHER INFORMATION: Sequence derived from the sequence SEQ ID NO: 1

<400> SEQUENCE: 7

Ala Ile Trp Gln Cys Thr Val Cys Gly Tyr Lys Tyr Asp Glu Asp Lys
1               5                   10                  15

Glu Lys Lys Lys Phe Glu Asp Leu Pro Ala Asp Tyr Lys Cys Pro Val
                20                  25                  30

Cys Gly Ala Lys Lys Glu Met Phe Lys Lys Ser
            35                  40

<210> SEQ ID NO 8
<211> LENGTH: 72
<212> TYPE: PRT
<213> ORGANISM: Podospora anserina
<220> FEATURE:
<221> NAME/KEY: PEPTIDE
<222> LOCATION: (1)..(72)
<223> OTHER INFORMATION: Residues 218 to 289 of the protein Het-s

<400> SEQUENCE: 8

Lys Ile Asp Ala Ile Val Gly Arg Asn Ser Ala Lys Asp Ile Arg Thr
1               5                   10                  15

Glu Glu Arg Ala Arg Val Gln Leu Gly Asn Val Val Thr Ala Ala Ala
                20                  25                  30

Leu His Gly Gly Ile Arg Ile Ser Asp Gln Thr Thr Asn Ser Val Glu
            35                  40                  45

Thr Val Val Gly Lys Gly Glu Ser Arg Val Leu Ile Gly Asn Glu Tyr
        50                  55                  60

Gly Gly Lys Gly Phe Trp Asp Asn
65                  70

<210> SEQ ID NO 9
<211> LENGTH: 117
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(117)
<223> OTHER INFORMATION: Chimeric protein formed by the sequences SEQ ID
      NO: 6 and SEQ ID NO: 13
```

```
<400> SEQUENCE: 9

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Tyr Lys Cys Pro
                20                  25                  30

Val Cys Gly Ala Lys Lys Glu Met Phe Lys Lys Ser Met Glu Ile Asp
            35                  40                  45

Ala Ile Val Gly Arg Asn Ser Ala Lys Asp Ile Arg Thr Glu Glu Arg
    50                  55                  60

Ala Arg Val Gln Leu Gly Asn Val Val Thr Ala Ala Leu His Gly
65                  70                  75                  80

Gly Ile Arg Ile Ser Asp Gln Thr Thr Asn Ser Val Glu Thr Val Val
                85                  90                  95

Gly Lys Gly Glu Ser Arg Val Leu Ile Gly Asn Glu Tyr Gly Gly Lys
                100                 105                 110

Gly Phe Trp Asp Asn
            115

<210> SEQ ID NO 10
<211> LENGTH: 123
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(123)
<223> OTHER INFORMATION: Chimeric protein derived from the sequence SEQ
      ID NO: 9

<400> SEQUENCE: 10

Met Ala Ile Trp Gln Cys Thr Val Cys Gly Tyr Lys Tyr Asp Glu Asp
1               5                   10                  15

Lys Glu Lys Lys Lys Phe Glu Asp Leu Pro Ala Asp Tyr Lys Cys Pro
                20                  25                  30

Val Cys Gly Ala Lys Lys Glu Met Phe Lys Lys Ser Met Glu Ile Asp
            35                  40                  45

Ala Ile Val Gly Arg Asn Ser Ala Lys Asp Ile Arg Thr Glu Glu Arg
    50                  55                  60

Ala Arg Val Gln Leu Gly Asn Val Val Thr Ala Ala Leu His Gly
65                  70                  75                  80

Gly Ile Arg Ile Ser Asp Gln Thr Thr Asn Ser Val Glu Thr Val Val
                85                  90                  95

Gly Lys Gly Glu Ser Arg Val Leu Ile Gly Asn Glu Tyr Gly Gly Lys
                100                 105                 110

Gly Phe Trp Asp Asn His His His His His
            115                 120

<210> SEQ ID NO 11
<211> LENGTH: 240
<212> TYPE: DNA
<213> ORGANISM: Artificial Sequence
<220> FEATURE:
<223> OTHER INFORMATION: Synthesized sequence
<220> FEATURE:
<221> NAME/KEY: CDS
<222> LOCATION: (1)..(240)
<223> OTHER INFORMATION: Nucleotide sequence encoding the sequence SEQ
      ID NO: 13

<400> SEQUENCE: 11
```

```
atggagatcg acgcgattgt gggaaggaat tccgccaagg atatcagaac agaggaacgt      60
gcaagggtcc agctcggcaa tgttgtcact gcggcagccc tacatggtgg gatccgtatc     120
agcgaccaga caaccaactc ggtagagacg gttgtgggga agggcgagtc tagggtcctt     180
attggaaatg agtacggagg taaggggttc tgggataatc accatcacca tcatcactaa    240
```

```
<210> SEQ ID NO 12
<211> LENGTH: 132
<212> TYPE: DNA
<213> ORGANISM: Artificial Sequence
<220> FEATURE:
<223> OTHER INFORMATION: Synthesized sequence
<220> FEATURE:
<221> NAME/KEY: CDS
<222> LOCATION: (1)..(132)
<223> OTHER INFORMATION: Nucleotide sequence encoding the sequence SEQ
      ID NO: 6

<400> SEQUENCE: 12
```

```
atggcgatct ggcagtgtac cgtttgcggt tacaaatacg atgaagataa agaaaagaaa      60
aaatttgaag acctgccggc ggattacaaa tgtccggttt gcggtgcgaa aaagaaatg     120 tttaagaaat cc                                                         132
```

```
<210> SEQ ID NO 13
<211> LENGTH: 73
<212> TYPE: PRT
<213> ORGANISM: Artificial Sequence
<220> FEATURE:
<223> OTHER INFORMATION: Synthesized sequence
<220> FEATURE:
<221> NAME/KEY: PEPTIDE
<222> LOCATION: (1)..(73)
<223> OTHER INFORMATION: Sequence derived from the sequence SEQ ID NO: 8

<400> SEQUENCE: 13
```

```
Met Glu Ile Asp Ala Ile Val Gly Arg Asn Ser Ala Lys Asp Ile Arg
1               5                   10                  15

Thr Glu Glu Arg Ala Arg Val Gln Leu Gly Asn Val Val Thr Ala Ala
            20                  25                  30

Ala Leu His Gly Gly Ile Arg Ile Ser Asp Gln Thr Thr Asn Ser Val
        35                  40                  45

Glu Thr Val Val Gly Lys Gly Glu Ser Arg Val Leu Ile Gly Asn Glu
    50                  55                  60

Tyr Gly Gly Lys Gly Phe Trp Asp Asn
65                  70
```

UNITED STATES PATENT AND TRADEMARK OFFICE
CERTIFICATE OF CORRECTION

PATENT NO.        : 9,550,810 B2                                   Page 1 of 1
APPLICATION NO.   : 14/003560
DATED             : January 24, 2017
INVENTOR(S)       : Vincent Forge et al.

It is certified that error appears in the above-identified patent and that said Letters Patent is hereby corrected as shown below:

In the Specification

Column 7, Line 31: "in position of this" should be --in position 29 of this--.

Signed and Sealed this
Seventh Day of March, 2017

Michelle K. Lee
*Director of the United States Patent and Trademark Office*